US008663086B2

(12) United States Patent
Duncan et al.

(10) Patent No.: US 8,663,086 B2
(45) Date of Patent: Mar. 4, 2014

(54) MEDICAL REINFORCEMENT GRAFT

(75) Inventors: Mark Duncan, Westfield, IN (US);
Christopher M. Nelson, Lafayette, IN (US); F. Joseph Obermiller, West Lafayette, IN (US); Bhavin Shah, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 422 days.

(21) Appl. No.: 12/892,123

(22) Filed: Sep. 28, 2010

(65) Prior Publication Data

US 2011/0077455 A1  Mar. 31, 2011

Related U.S. Application Data

(60) Provisional application No. 61/246,413, filed on Sep. 28, 2009, provisional application No. 61/312,701, filed on Mar. 11, 2010.

(51) Int. Cl.
*A61F 2/02* (2006.01)
(52) U.S. Cl.
USPC ............................................ 600/30
(58) Field of Classification Search
USPC ................................. 600/29, 30
See application file for complete search history.

(56) References Cited

U.S. PATENT DOCUMENTS

| 2,127,903 | A | 3/1938 | Bowen |
| 2,167,251 | A | 7/1939 | Rogers |
| 3,272,204 | A | 9/1966 | Artandi |
| 4,321,914 | A | 3/1982 | Begovac et al. |
| 4,781,176 | A | 11/1988 | Ravo |
| 4,801,299 | A | 1/1989 | Brendel et al. |
| 4,902,508 | A | 2/1990 | Badylak et al. |
| 4,956,178 | A | 9/1990 | Badylak |
| 4,969,902 | A | 11/1990 | Ravo |
| 5,269,774 | A | 12/1993 | Gray |
| 5,281,422 | A | 1/1994 | Badylak et al. |
| 5,554,389 | A | 9/1996 | Badylak et al. |
| 5,934,283 | A * | 8/1999 | Willem et al. ............... 128/885 |
| 5,955,110 | A | 9/1999 | Patel et al. |
| 6,099,567 | A | 8/2000 | Badylak et al. |
| 6,206,931 | B1 | 3/2001 | Cook et al. |
| 6,475,232 | B1 | 11/2002 | Babbs et al. |
| 8,172,745 | B2 * | 5/2012 | Rosenblatt ..................... 600/30 |
| 2006/0195011 | A1 * | 8/2006 | Arnal et al. ..................... 600/37 |
| 2007/0166395 | A1 * | 7/2007 | McAlexander et al. ...... 424/551 |
| 2009/0125119 | A1 * | 5/2009 | Obermiller et al. ........ 623/23.65 |

* cited by examiner

*Primary Examiner* — Charles A Marmor, II
*Assistant Examiner* — Thaddeus Cox
(74) *Attorney, Agent, or Firm* — Woodard, Emhardt, Moriarty, McNett & Henry LLP

(57) ABSTRACT

The embodiments described include graft devices for reinforcing patient tissue structures and methods of making and using the graft devices. In certain embodiments the graft devices have a remodelable extracellular matrix material graft body defining a slot and having a portion receivable through the slot to form a closed loop. Such graft devices can be used in encircling reinforcement of patient tissue structures such as anal sphincters or anastomosed vessel segments.

8 Claims, 3 Drawing Sheets

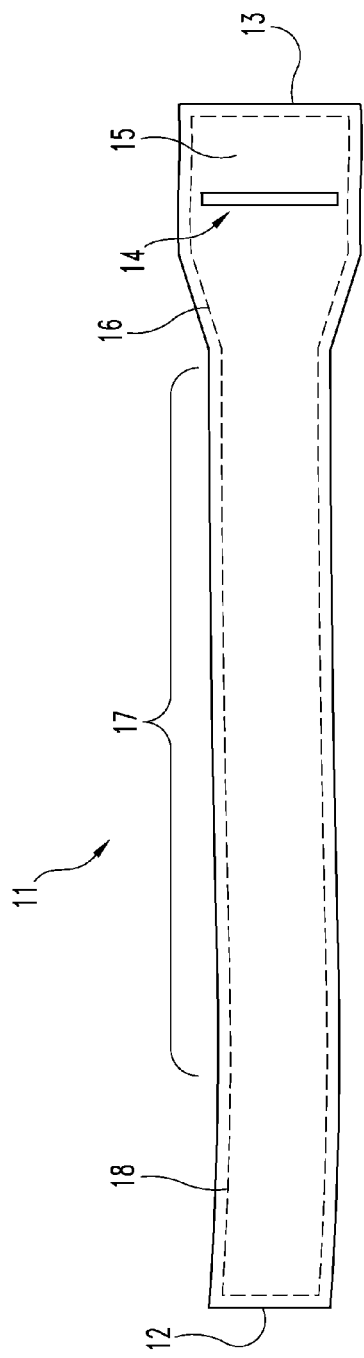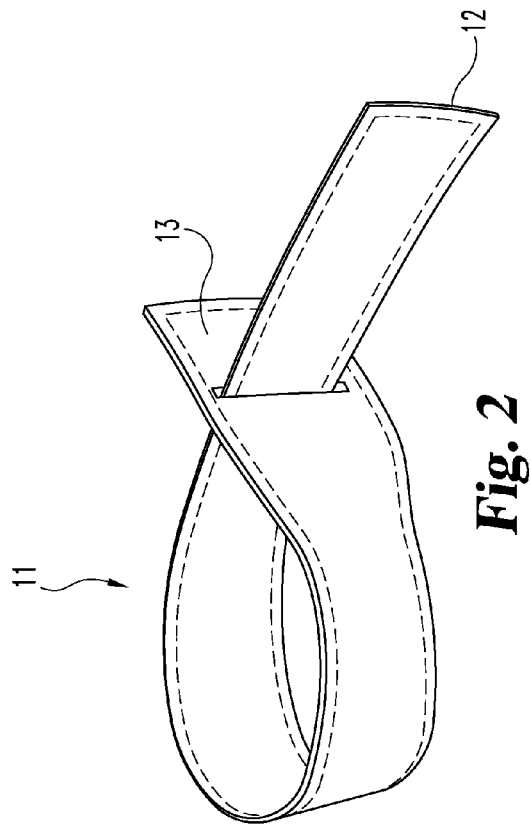

MEDICAL REINFORCEMENT GRAFT

REFERENCE TO RELATED APPLICATIONS

The present application claims the benefit of U.S. Provisional Patent Application Ser. No. 61/246,413, filed Sep. 28, 2009, and U.S. Provisional Patent Application Ser. No. 61/312,701, filed Mar. 11, 2010, both entitled "MEDICAL REINFORCEMENT GRAFT", each of which are hereby incorporated by reference in their entirety.

BACKGROUND

The present invention relates to generally to medical devices, and in particular to medical devices for reinforcing tissue structures.

As further background, it is often necessary to provide reinforcement for patient tissues. In certain cases, the involved tissue structures call for circumferential reinforcement. Illustratively, in some cases of weakness or other impairment of tissues in the rectal area, commonly causing incontinence, it is helpful to reinforce the rectal tissues to support and potentially resize the rectal opening. In still other instances, tissues of tubular organs such as the intestine, stomach, or esophagus, are sutured or otherwise attached to adjacent tissues to form a fluid-tight connection. As examples, end-to-end anastomoses are commonly performed in gastric or intestinal surgery.

Needs remain for medical devices and methods to facilitate tissue reinforcement.

SUMMARY

Provided in one embodiment is a tissue reinforcement graft. The graft has an elongate body, desirably comprised of a remodelable extracellular matrix tissue material. The elongate graft body defines a slit. One end of the graft body is receivable through the slit to form a closed loop for encircling patient tissue. The slit can have a slit width that is approximately equal to or greater than the width of a portion of the graft body to be received though the slit. In this fashion, the graft can be manipulated to its closed loop configuration with minimal or no rolling, bunching or folding of the graft material as it passes through the slit. The slit can be provided in a graft body portion having a width that is greater than the width of the slit and greater than the width of the graft body portion configured for receipt through the slit. In certain embodiments, the graft body can have a first elongate portion for receipt through the slit, wherein the first elongate portion has a substantially constant width along its length. The graft body in this embodiment can have a second portion in which the slit is located, with the width of the second portion being greater than that of the first portion. The graft body in this embodiment can have a tapered portion tapering in width and connecting the first graft body portion to the second graft body portion. The second graft body portion can have length that is less than the length of the first graft body portion.

In certain other embodiments, provided are methods for reinforcing patient tissue. The methods include providing a tissue reinforcement graft as discussed above and encircling a tissue structure of the patient with the reinforcement graft in a closed loop configuration. The closed loop configuration can be adjusted to the desired size and fixed to that size, for example by connecting overlapping portions of the graft body to each other and/or adjacent patient tissues. In certain embodiments, the patient tissue that is reinforced is in the rectal area of a patient, and in particular the reinforcement graft can be used to encircle the anal sphincter complex of a patient, for example to reinforce and potentially resize the anal opening to enhance or improve continence in the patient.

Additional embodiments of the invention as well as their features and advantages will be apparent from the descriptions herein.

BRIEF DESCRIPTION OF THE DRAWINGS

FIG. 1 provides a planned view of one tissue reinforcement graft embodiment of the invention.

FIG. 2 provides a prospective view of the graft of FIG. 1 in a closed loop configuration.

DETAILED DESCRIPTION

Figure 3A:
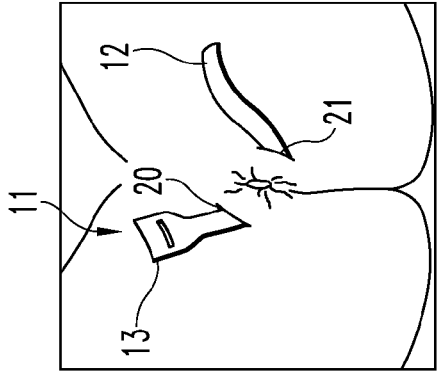
FIGS. 3A-3D provide illustrations of various stages of a surgical procedure using the graft of FIG. 1 to encircle and reinforce the anal sphincter complex.
Figure 3B:
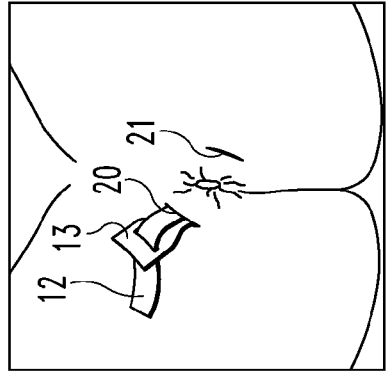
Figure 3C:
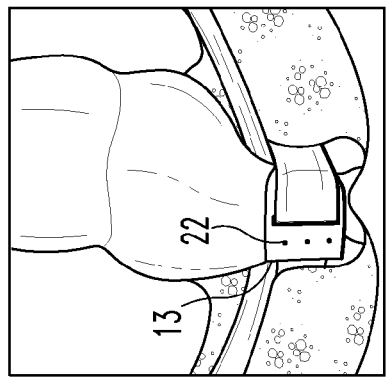
Figure 3D:
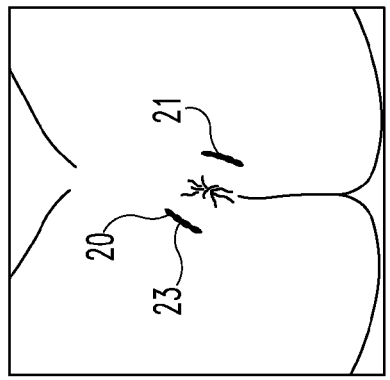

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As disclosed above, the present invention relates to medical tissue reinforcement grafts and methods of their manufacture and use. With reference now to FIG. 1, shown is a plan view of one embodiment of a reinforcement graft 11, having a first end 12 and a second end 13. Graft 11 defines an elongate slit or slot 14, sized for sliding passage of graft first end 12 therethrough, and preferably situated transverse to the longitudinal axis of graft 11, more preferably substantially perpendicular to such longitudinal axis. Slot 14 is defined within a portion 15 of graft 11 having a width that is greater than the width of first end 12. Graft 11 includes a tapered portion 16 from which wider graft portion 15 tapers to a smaller width portion 17, desirably of constant or substantially constant diameter. Portion 17 is passable through slot 14 without rolling or folding of portion 17. In this manner, graft device 11 can be sized in its closed loop configuration to various loop dimensions in which a region of graft portion 17 contacts slot 14 without the need for bunching or folding in the receipt of such region through slot 14. In this fashion, graft 11 can be used to encircle and support patient tissue while maintaining graft 11 in a substantially plainer or ribbon-like configuration. Graft 11 in such condition can thus be essentially free from any bunches or folds and can provide a more even and broader distribution of support for the patient tissue. Graft 11 also includes a line of reinforcement sutures 18 traversing the perimeter of the graft 11 proximate to its outermost periphery. Reinforcing suture line 18 is useful for example in embodiments in which graft 11 is made of multiple stacked and potentially bonded sheets of graft material.

With reference to FIG. 2, shown is graft 11 in its closed loop configuration. As can be seen, graft end 12 has been received through slot 14 to form a closed loop in which the diameter of the loop portion can be adjusted by varying how far end 12 is received through slot 14. Graft 11 is sufficiently pliable to enable manual manipulation from a non-closed condition, preferably substantially planar, to such a closed loop configuration.

With reference now to FIGS. 3A to 3D, shown are illustrations of various stages of a surgical procedure using graft 11 to reinforce tissues in the rectal area of a patient. In one surgical embodiment, which can be performed under regional or general anesthesia, a first incision 20 is made anteriorly outside of the anal verge, and a second incision 21 is made posteriorly outside of the anal verge. The first incision 20 can be greater in length than the second incision 21, with these incisions for example having lengths of about 2 cm and 1 cm respectively. Incisions 20 and 21 can then be used for access to bluntly dissect a tunnel around the anal sphincter complex, and the created tunnel can be irrigated with saline or an antimicrobial solution. The dissected tunnel around the anal sphincter complex is preferably within the ischiorectal fossae plane. Using the sterile techniques, graft 11 can be manipulated in the surgical environment and hydrated, whereupon in the case of a hydratable remodelable ECM graft, the graft typically becomes more supple. Using aseptic technique, the first end 12 of the graft 11 is passed into the first incision 20, through a portion of the dissected encircling tunnel, and out of the second incision 21. The first end 12 is then reversed and passed back into incision 21 and then through the remaining portion of the tunnel and back out of the first incision 20. First end 12 is then passed through slot 14 of graft 11 to convert the graft 11 to its closed loop configuration with the loop encircling the anal sphincter complex. In its closed loop configuration, the graft 11 is positioned and tightened using a "buckle" technique, pulling the end 12 through the slot 14. If desired, an instrument can be placed within the anal opening during this tightening procedure to serve as a guide and protect against an undesired level of size reduction of the opening. The graft 11 is then connected to itself under the desired tension in order to fix the graft in its closed loop condition. This can be accomplished, for example, by inserting a plurality of sutures or staples 22 though the enlarged region 15 and through the region of elongate portion 17 layered against the enlarged region 15 in the closed loop configuration. The excess graft portion pulled through the slot 14 can then be trimmed a distance from the suture or staple line, for example at least about 5 mm after the staple line, to provide adequate material to resist a pull through of the sutures or staples. Proper device placement and appropriate anal canal diameter can then be confirmed and the areas surrounding the cutaneous openings can be cleaned and treated with an anti bacterial ointment. The incisions 20 and 21 can then be closed using standard technique, for example using sutures or staples 23. These closures can be done loosely in order to allow for drainage, and appropriate dressings applied. Where the graft device 11 is made with a remodelable ECM tissue material as described herein, tissue ingrowth and remodeling of the device can provide an encircling ring of new tissue of the patient which surrounds and reinforces the sphincter complex. Further, remodelable ECM tissue materials as described herein are conducive to tissue ingrowth, which can assist in fixing the graft device 11 in place from a point in time early in the remodeling phase, which in turn can enhance migration resistance of the device under forces and movements in the region of the anal sphincter.

In other uses, reinforcement graft 11 can be used to surround an end-to-end or an end-to-side anastomosis of two bodily vessel segments, for example connecting segments of the large or small intestine, the stomach, or the esophagus. The anastomosis may for example exist as a component of a bariatric surgery conducive to weight loss, such as a gastric bypass. The anastomosis connection of the segments can be created using sutures, staples, or any other appropriate device or technique. Thereafter, graft 11 can be manipulated to its closed condition surrounding the anastomosis, tightened in the "buckle" fashion described above, and secured and trimmed as described above to reinforce the anastomosis. Where the graft device 11 is made with a remodelable material as described herein, tissue ingrowth and remodeling of the device can provide a cuff of new tissue of the patient which surrounds and reinforces the anastomosis and potentially also provides an additional measure of protection against leaks.

Figure 4:
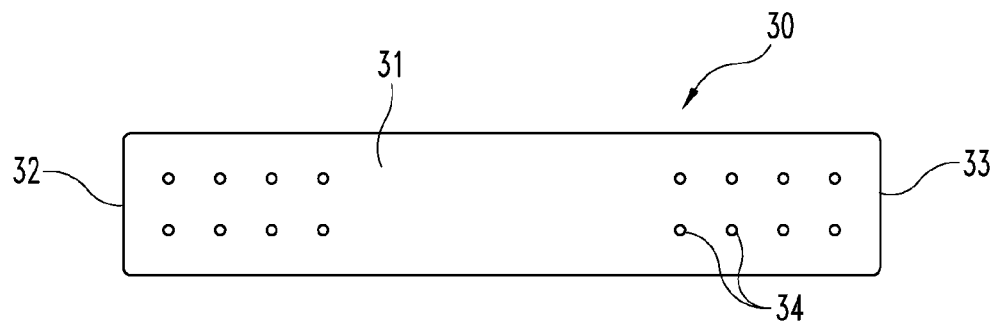
FIG. 4 provides a planned view of another tissue reinforcement graft embodiment of the invention.

With reference now to FIG. 4, shown is a plan view of a reinforcement graft 30 according to another embodiment of the invention. Graft 30 includes a length of material 31 having a first end 32 and a second end 33. While substantially rectangular in this specific illustrative embodiment, such an elongated segment can be shaped and configured in a variety of manners, for example, having rectilinear and/or curvilinear features along one or more sides of the material. The length of material 31 is outfitted with multiple holes 34 which are arranged in non-random rows near each end of the graft. While optional, when these types of holes or passages are incorporated into an inventive graft, they can vary in number and positioning along the graft. Additionally, while the illustrated holes each provide an opening that extends completely through the material, in alternative forms, a hole will instead provide an opening or indentation in an outer surface of the material that does not extend entirely through the graft. Such an opening or indentation can be formed in a variety of manners. Illustratively, a multilayer graft can include an outer layer that has hole in it and an underlying layer without a hole so as to provide a reduced thickness region of the graft material at the location of the hole. Such a reduced thickness region can facilitate an easier entry and passage of a needle, staples, etc. through the material without having to necessarily incorporate a full thickness opening into a graft material.

Graft 30 can be used to fully or partially surround and support various tissue structures. In some forms, opposing ends of the graft will be made to overlap one another so that the graft fully encircles an amount of patient tissue. The graft material can then be secured to itself in any number of fashions as discussed herein. While not necessary to broader aspects of the embodiment, as the rows are arranged in FIG. 4, it is possible to overlap opposing ends of the graft 30 with one set of holes from the first end of the graft being aligned with another set of holes from the second end of the graft so as to place the graft into one of several closed loop configurations having different circumferences. The graft material can then be secured in a closed loop condition, e.g., by inserting a plurality of sutures or staples though one or more of the holes.

Figure 5:
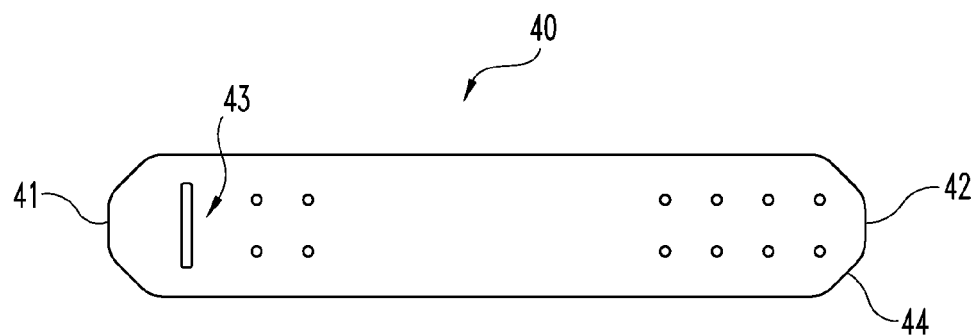
FIG. 5 provides a planned view of still another tissue reinforcement graft embodiment of the invention.

With reference now to FIG. 5, shown is a plan view of a reinforcement graft 40 according to another embodiment of the invention. Graft 40 has a first end 41 and a second end 42, and defines an elongate slit or slot 43, preferably situated transverse to the longitudinal axis of graft 40, more preferably substantially perpendicular to such longitudinal axis, which is adapted to receive graft first end 41 therethrough. Graft 40 is substantially rectangular with beveled corner regions 44 that connect adjacent sides and ends of the graft. While optional, when these types of modified corner regions are incorporated into an inventive graft, they can be shaped and configured in a variety of manners, for example, as seen in some designs where an elongate graft includes a curved or non-curved tapered region along one or more edges of the graft. Beveling the corners, or otherwise narrowing the material near the end of the graft, can facilitate passage of the graft material through a tissue environment, for example, when a substantially dry graft segment is advanced through a dissected tunnel around an anal sphincter complex. Providing a narrowed region near the end of the graft can also facilitate slidable receipt of the graft second end through slot 43 when forming a closed loop configuration.

Slot 43 is shown having a smaller width than other portions of the graft. Thus, while part of the second end 42 might be made the same or slightly less than the width of slot 43 (e.g., to facilitate slidable receipt of the second end 42 through the slot), in some preferred forms, material near the graft second end will be made somewhat wider than the slot so that when the second end 42 is received through slot 43 to place the graft 40 into a closed loop configuration, the comparatively oversized material will be forced to roll and/or fold over itself while moving through the slot so as to provide a friction-type fit between the boundaries of the slot and the graft material. Such a friction-type fit, even if only effective for a temporary hold, can free a surgeons hand to allow for a more efficient encircling procedure. This illustrative graft is also outfitted with non-random groupings of holes near each end of the graft.

Figure 6:
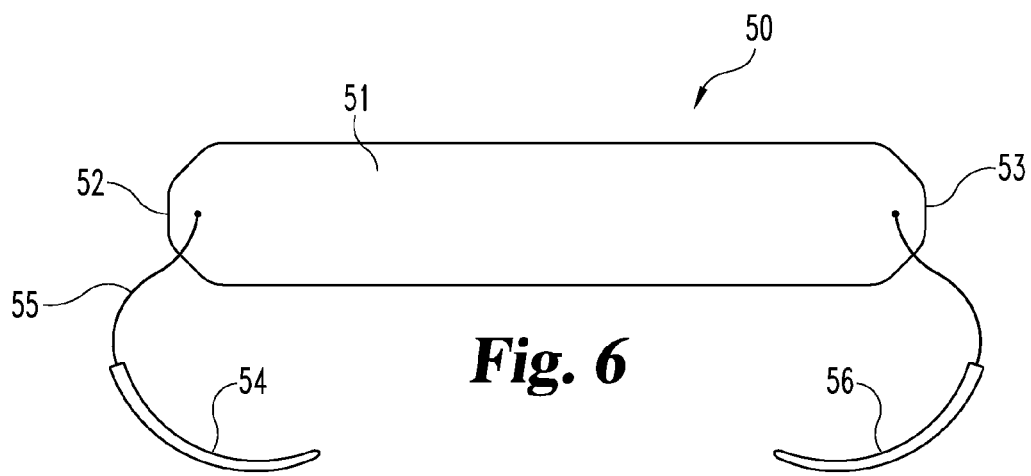
FIG. 6 provides a planned view of yet another tissue reinforcement graft embodiment of the invention.

With reference now to FIG. 6, shown is a plan view of a reinforcement system 50 according to one embodiment of the invention. System 50 includes a length of graft material 51 having a first end 52 and a second end 53. Graft material 50 is substantially rectangular with beveled corner regions connecting adjacent edges of the material, though the graft can be alternatively shaped as discussed elsewhere herein. System 50 further includes a first tissue penetrating member 54 which exhibits a degree of curvature and has a blunt nose or tip. Tissue penetrating member 54 is connected to graft material 50 near the first end 52 of the material by a length of suture material 55. In some alternative forms, a tissue penetrating member will be coupled directly to the graft material. System 50 further includes a second tissue penetrating member 56 connected via a suture to graft material 50 near its second end 53.

In one illustrative method, system 50 is used in a surgical procedure to reinforce tissues in the rectal area of a patient. The leading end of the first tissue penetrating member 54 is passed through a first incision (e.g., made anteriorly outside of the anal verge) and used to bluntly dissect a tunnel around a first side of the anal sphincter complex. The tissue penetrating member, in this particular embodiment, is eventually removed from the tunnel through a second incision (e.g., made posteriorly outside of the anal verge) and dissociated from the graft material. By tunneling and advancing the tissue penetrating member in this manner, the user can successfully deliver a portion of the graft material into the first side tunnel by drawing the graft first end 52 into the tunnel through the first incision and advancing it toward the second incision, with the beveled corner regions potentially facilitating passage of the graft material through the dissected tunnel. In an alternative embodiment, the tissue penetrating member and trailing graft material will be passed through a pre-formed tunnel (e.g., one that was previously bluntly dissected).

Continuing with the current method, the second tissue penetrating member 56 is also inserted into the first incision; however, it is used to bluntly dissect a tunnel around the opposite (second) side of the anal sphincter complex. Using this approach, a portion of the graft material can be successfully delivered to the second side tunnel by drawing the graft second end 53 into the tunnel through the first incision and advancing it toward the second incision. With both graft ends eventually located at or near the second incision, a variety of direct and indirect connections can be made between the two to provide a closed loop structure encircling the anal sphincter complex. In some instances, at least a portion of the connecting suture 55 will be retained on the graft after the tissue penetrating member has been removed, with the retained suture being used to help secure the graft material to itself and/or surrounding tissues. While it is not required that either graft end be removed from the tunneled region to complete a full or substantial encirclement of the anal sphincter complex, in a preferred embodiment, both graft ends will be at least temporarily withdrawn from the tunneled region through the second incision and further manipulated to form a closed loop structure encircling the anal sphincter complex.

In an alternative embodiment, an inventive system includes an elongate graft material associated with a single tissue penetrating member. In an illustrative method of using such a system to reinforce tissues in the rectal area of a patient, a first incision is made anteriorly outside of the anal verge, and a second incision is made posteriorly outside of the anal verge. A first end of the graft material (trailing the tissue penetrating member) is drawn through the first incision, through a tunnel extending generally around one side of the anal sphincter complex between the first incision and the second incision, and out of the second incision. Still trailing the tissue penetrating member, the first end of the graft material is then reversed and drawn back through the second incision, through a tunnel extending generally around the other side of the anal sphincter complex between the second incision and the first incision, and toward the first incision. A connection will be made between the first graft end and the second graft end at or near the first incision to provide a closed loop structure encircling the anal sphincter complex. In some instances, a sufficiently long piece or graft material will be used to allow for one or more additional passes of the graft material through a tunneled region, for example, in procedures where the graft material is made to generally encircle the anal sphincter complex one to six times or more, e.g., 1.5, 2.0, 2.5, 3.0, 3.5 or 4.0 times.

Reinforcement graft devices of the invention can be made from extracellular matrix (ECM) tissue. The ECM tissue can be obtained from a warm-blooded vertebrate animal, such as an ovine, bovine or porcine animal. For example, suitable ECM tissue include those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. ECM tissues comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. Porcine tissue sources are preferred sources from which to harvest ECM tissues, including submucosa-containing ECM tissues.

The ECM tissue used in the invention is preferably decellularized and highly purified, for example, as described in U.S. Pat. No. 6,206,931 to Cook et al. or U.S. Patent Application Publication No. US2008286268 dated Nov. 20, 2008, publishing U.S. patent application Ser. No. 12/178,321 filed Jul. 23, 2008, all of which are hereby incorporated herein by reference in their entirety. Preferred ECM tissue material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 or U.S. Patent Application Publication No. US2008286268 may be characteristic of any ECM tissue used in the present invention.

In certain embodiments, the ECM tissue material used in the manufacture of the reinforcement graft will be a membranous tissue with a sheet structure as isolated. The ECM tissue can, as isolated, have a layer thickness that ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue material utilized desirably retains a structural microarchitecture from the source tissue, including structural fiber proteins such as collagen and/or elastin that are non-randomly oriented. Such non-random collagen and/or other structural protein fibers can in certain embodiments provide an ECM tissue that is non-isotropic in regard to tensile strength, thus having a tensile strength in one direction that differs from the tensile strength in at least one other direction.

The ECM tissue material may include one or more bioactive agents native to the source of the ECM tissue material and retained in the ECM tissue material through processing. For example, a submucosa or other remodelable ECM tissue material may retain one or more native growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain from the source tissue one or more bioactive components that induce, directly or indirectly, a cellular response such as a change in cell morphology, proliferation, growth, protein or gene expression.

Submucosa-containing or other ECM materials used in the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM tissue material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

When used in the invention, ECM materials can be free or essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Remodelable ECM tissue materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, the body of the reinforcement graft can exhibit substantial porosity. In certain embodiments, the porosity of a layer of ECM tissue material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

The reinforcement graft can be made from a plurality of stacked or overlapped layers of an ECM tissue as described herein. Such multilaminate structures when used in the invention can include a plurality of ECM tissue material layers bonded together. Illustratively, two or more ECM segments can be fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. A combination of one or more of these with dehydration-induced bonding may also be used to bond ECM material layers to one another.

In preferred embodiments, multiple layers or other pieces of ECM material are bonded to on another under dehydrating conditions to make a multilaminate construct. The term "dehydrating conditions" can include any mechanical or environmental condition which promotes or induces the removal of water from the ECM material. To promote dehydration of the compressed ECM material, any surface(s) compressing the layers of ECM material during dehydration can be water permeable. Dehydration of the ECM material can optionally be further enhanced by applying blotting material, heating the matrix structure or blowing air, or other inert gas, across the exterior of any compressing surface(s). One particularly preferred method of dehydration bonding ECM materials is lyophilization of the ECM layers stacked onto and in contact with each other, e.g. by freeze-drying or evaporative cooling conditions. Such methods, when performed without compression of the ECM layers, leave a highly open porous matrix to the multilaminate ECM construct, making a reinforcement graft made from the material relatively supple and conducive to cellular invasion and remodeling.

Another method of dehydration bonding comprises pulling a vacuum on the multi-layer ECM assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is sometimes advantageous to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In certain embodiments, a reinforcement graft comprised of a multilaminate ECM construct having layers with surfaces bonded to one another, also has sutures passed through and holding the layers together. For example, as illustrated in the Figures, a continuous suture line is provided around the perimeter of the graft proximate to its outer periphery. Such a suture reinforcement can assist in maintaining the general structural integrity of the device should any delamination of the bonded layer surfaces occur. The sutures, or other connectors such as staples passed through the layers to similarly reinforce the graft, can be persistent or bioresorbable when implanted in the patient. Bioresorbable materials, for example polymers of lactic acid and/or glycolic acid, are preferred for these purposes.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method for reinforcing an anal sphincter around an anal opening of a patient, comprising:
   providing an elongate graft structure having a graft body comprised of membranous extracellular matrix tissue harvested from a source tissue of warm-blooded vertebrate animal and decellularized, the membranous extracellular matrix material having structural protein fibers retained in a non-random orientation that existed in said source tissue, said elongate graft structure having a first end and a second end;
   making a first skin incision generally to a first side of the anal opening;
   making a second skin incision generally to a second side of the anal opening;
   dissecting a tunnel around the anal sphincter;
   introducing the first end of the graft structure into the first skin incision;
   after said introducing, first advancing the first end of the graft structure under the skin to and out of the second skin incision, said advancing partially circumscribing said tunnel with said graft structure, leaving a remainder of said tunnel to be circumscribed by said graft structure;
   after said first advancing, inserting the first end of the graft structure back into the second skin incision;
   after said inserting, second advancing the first end of the graft structure under the skin to and out of said first skin incision, said second advancing circumscribing the remainder of said tunnel with said graft structure;
   passing said first end through an opening in said graft structure to create a closed loop of the graft structure; and
   tightening said closed loop of the graft structure to reinforce the anal sphincter.

2. The method of claim 1, wherein said membranous extracellular matrix tissue becomes completely remodeled and replaced by tissue of the patient.

3. The method of claim 1, wherein said membranous extracellular matrix tissue comprises submucosal tissue.

4. The method of claim 1, wherein said elongate graft structure comprises a multilaminate construct having multiple layers of the membranous extracellular matrix tissue.

5. A method for reinforcing an anal sphincter around an anal opening of a patient, comprising:
   providing an elongate graft structure having a graft body comprised of membranous extracellular matrix tissue harvested from a source tissue of warm-blooded vertebrate animal and decellularized, the membranous extracellular matrix material having structural protein fibers retained in a non-random orientation that existed in said source tissue, said elongate graft structure having a first end and a second end;
   making a first skin incision generally to a first side of the anal opening;
   making a second skin incision generally to a second side of the anal opening;
   dissecting a first portion of a tunnel around the anal sphincter, said first portion extending between said first skin incision and said second skin incision;
   dissecting a second portion of said tunnel around the anal sphincter, said second portion extending between said first skin incision and said second skin incision opposite said first portion;
   introducing the first end of the graft structure into the first skin incision;
   after said introducing, first advancing the first end of the graft structure under the skin through said first portion, and out of the second skin incision, said advancing partially encircling the anal sphincter with said graft structure;
   after said first advancing, inserting the first end of the graft structure back into the second skin incision;
   after said inserting, second advancing the first end of the graft structure under the skin through said second portion, and out of said first skin incision, said second advancing encircling the remainder of the anal sphincter with said graft structure; and
   securing said graft structure in a closed loop to reinforce the anal sphincter.

6. The method of claim 5, wherein said membranous extracellular matrix tissue becomes completely remodeled and replaced by tissue of the patient.

7. The method of claim 5, wherein said membranous extracellular matrix tissue comprises submuco sal tissue.

8. The method of claim 5, wherein said securing step comprises inserting one or more sutures through said first end and said second end.

* * * * *